United States Patent
Cai et al.

(10) Patent No.: US 11,587,270 B2
(45) Date of Patent: Feb. 21, 2023

(54) METHOD AND SYSTEM FOR RECONSTRUCTION OF CEST CONTRAST IMAGE

(71) Applicant: Xiamen University, Fujian (CN)

(72) Inventors: Shuhui Cai, Fujian (CN); Chenlu Guo, Fujian (CN); Congbo Cai, Fujian (CN); Jian Wu, Fujian (CN)

(73) Assignee: XIAMEN UNIVERSITY, Xiamen (CN)

( * ) Notice: Subject to any disclaimer, the term of this patent is extended or adjusted under 35 U.S.C. 154(b) by 242 days.

(21) Appl. No.: 17/100,114

(22) Filed: Nov. 20, 2020

(65) Prior Publication Data

US 2021/0158581 A1    May 27, 2021

(51) Int. Cl.
| | | |
|---|---|---|
| *G06T 11/00* | (2006.01) | |
| *G16H 50/50* | (2018.01) | |
| *G16H 30/40* | (2018.01) | |
| *G06K 9/62* | (2022.01) | |
| *G06N 3/08* | (2023.01) | |

(52) U.S. Cl.
CPC .......... *G06T 11/006* (2013.01); *G06K 9/6256* (2013.01); *G06N 3/08* (2013.01); *G06T 11/001* (2013.01); *G16H 30/40* (2018.01); *G16H 50/50* (2018.01); *G06T 2211/416* (2013.01)

(58) Field of Classification Search
CPC .......... G06T 2207/10088; G06T 2207/20081; G06T 2207/20084; G06T 7/11; G06T 2207/10096; G06T 2207/20016; G06T 2207/20104; G06T 5/009; G06T 7/0014; G06T 11/00; G06T 11/001; G06T 11/006; G06T 2207/30016; G06T 2207/30096; G06T 2211/416; G06T 7/0012; G16H 30/40; G16H 50/50
USPC ........................................................ 382/131
See application file for complete search history.

(56) References Cited

U.S. PATENT DOCUMENTS

| | | | |
|---|---|---|---|
| 2016/0022842 A1* | 1/2016 | Allen | A61K 9/127 534/15 |
| 2018/0268546 A1* | 9/2018 | Sun | G01R 33/5605 |
| 2020/0072931 A1* | 3/2020 | Zaiss | G06N 20/10 |

* cited by examiner

*Primary Examiner* — Ajibola A Akinyemi
(74) *Attorney, Agent, or Firm* — Nolte Lackenbach Siegel

(57) ABSTRACT

Disclosed is a method for reconstruction of a Chemical Exchange Saturation Transfer (CEST) contrast image. The method includes: generating training samples for a deep neural network; training the deep neural network with the training samples to obtain a trained deep neural network; and reconstructing a CEST contrast image by using the trained deep neural network and PROPELLER undersampled CEST images. The method for reconstruction of a CEST contrast image can effectively shorten the experimental time of a CEST contrast imaging and can obtain a smoother and more accurate CEST contrast image. Further disclosed is a system for reconstruction of a CEST contrast image to implement the method for reconstruction.

7 Claims, 3 Drawing Sheets

METHOD AND SYSTEM FOR RECONSTRUCTION OF CEST CONTRAST IMAGE

CROSS REFERENCE TO RELATED APPLICATION

This application claims the priority of Chinese Patent Application No. CN201911173109.4, entitled "Method and System for Reconstruction of Cest Contrast Image" filed with the China National Intellectual Property Administration on Nov. 26, 2019, which is incorporated herein by reference in its entirety.

TECHNICAL FIELD

The disclosure relates to magnetic resonance imaging (MRI) technology, and in particular, to a method and system for reconstruction of a Chemical Exchange Saturation Transfer (CEST) contrast image based on Periodically Rotated Overlapping Parallel Lines with Enhanced Reconstruction (PROPELLER) and a deep neutral network.

BACKGROUND

CEST imaging can achieve quantitative characterization of chemical exchange between exchangeable protons and water protons in a protein or metabolite, providing a new contrast mechanism for MRI. The technique is an emerging molecular imaging technique, which serves to indirectly detect metabolite information by means of a water signal and thus can be used to detect some diseases, such as human cranial nervous system diseases, cerebral ischemia, tumors, etc., providing basis for disease diagnosis.

A general CEST imaging sequence includes a saturation module (continuous excitation pulse with long duration) and a signal readout module. Fast spin echo (FSE) or echo planar imaging (EPI) is typically used as the readout module. The FSE readout module can provide a high-quality CEST contrast image, but may take long scanning time to acquire data at a plurality of saturation frequency offsets, which severely restricts its application. The EPI readout module can save scanning time, but the obtained CEST contrast image may be distorted, leading to interference with a diagnosis result. At present, a lot of research groups have proposed some fast imaging sequences that are intended to solve the time-consuming problem of a CEST experiment by reducing signal acquisition time or obtaining multiple slices of CEST contrast images in one experiment, such as a multislice gradient echo method, CEST-FISP (CEST-Fast Imaging with Steady-state free Precession) method, and Radial UCI (Radial Ultrafast CEST Imaging) method. Such methods are all unsatisfactory in time-saving effect or sampling effect due to some objective limitations. For example, the multislice gradient echo method permits simultaneous acquisition of k-space data of different slices through one saturation. In essence, ineffective waiting time in the time of repetition (TR) of a pulse sequence is used to excite other slices, thus realizing multi-slice scanning. Therefore, this method does not shorten CEST scanning time, but allows for acquisition of multi-slice CEST signals in the same scanning time. The CEST-FISP method can shorten the scanning time, but the acquired signal has low signal-to-noise ratio. The Radial UCI method can shorten the scanning time, but is not suitable for a sample having a complex structure. In another aspect, there are also many methods proposed in research on calculation of a CEST contrast image via Z-spectrum fitting. Common methods include a higher-order polynomial fitting method, Bloch equation fitting method and Lorentzian equation fitting method. Such methods have respective limitations. For example, the higher-order polynomial fitting method is only suitable for data having a high signal-to-noise ratio. The Bloch equation fitting method is just suitable for a simple model, and for a complex model, the number of parameters in formulas may increase sharply, leading to decreases in algorithm efficiency and accuracy. Besides, the Lorentzian equation fitting method may be affected by magnetization transfer effect and noise, resulting in a large fitting error.

In conclusion, it is desirable to find a more effective method for rapid acquisition of a CEST contrast image. The new method is supposed to need just a little scanning time with short reconstruction time and high quality of a reconstructed CEST contrast image. Based on this, there is provided a CEST imaging technique based on PROPELLER and a deep neutral network.

SUMMARY

The disclosure aims to provide a method and system for reconstruction of a CEST contrast image that can allow for reconstruction of a high-quality CEST contrast image from undersampled data and reduction of the time needed for a CEST imaging experiment and the time for the reconstruction of the CEST contrast image.

To achieve the above objective, the disclosure provides the following solutions:

A method for reconstruction of a CEST contrast image, including:

S1: generating training samples for a deep neural network, which specifically includes the following steps:

S101: obtaining a simulated region;

S102: randomly generating in the simulated region a geometric figure that serves to simulate a part of an imaging object;

S103: setting parameters $\sigma_k$, $\omega_k$, $A_k$ and $\delta$ of the Lorentzian line shape model of CEST effect in the geometric figure separately to obtain a geometric figure with parameter $\sigma_k$, a geometric figure with parameter $\omega_k$, a geometric figure with parameter $A_k$, and a geometric figure with parameter $\delta$;

S104: adding filtered texture values and noise to the geometric figure with parameter $\sigma_k$, the geometric figure with parameter $\omega_k$, the geometric figure with parameter $A_k$, and the geometric figure with parameter $\delta$, where the texture values are used to simulate the texture of the imaging object, and the noise is used to simulate the noise during magnetic resonance (MR) sampling;

S105: repeating S102 to S104 until the random geometric figures overlay the whole simulated region, to obtain $\sigma_k$, $\omega_k$, $A_k$ and $\delta$ parameter maps in the Lorentzian line shape model of CEST effect, respectively;

S106: obtaining a combination of $\omega$ values in CEST imaging, where the combination of $\omega$ values is composed of a plurality of $\omega$ values, including a relatively large value corresponding to an unsaturated CEST image which is used for signal normalization;

S107: generating CEST images for each $\omega$ value by using the $\sigma_k$, $\omega_k$, $A_k$ and $\delta$ parameter maps in the Lorentzian line shape model of CEST effect;

S108: performing PROPELLER undersampling on the CEST images;

S109: combining the PROPELLER undersampled CEST images with the $A_k$ parameter map into a training sample; and S110: repeating S101 to S109 to generate a preset quantity of training samples;

S2: training the deep neural network by using the training samples to obtain a trained deep neural network; and S3: reconstructing a CEST contrast image by using the trained deep neural network and PROPELLER undersampled CEST images, which specifically includes the following steps:

acquiring CEST image data from an actual imaging object with a magnetic resonance imaging (MRI) sequence to obtain PROPELLER undersampled k-space data at the saturation frequency offsets corresponding to each ω value in the combination of ω values;

performing Fourier transformation on the PROPELLER undersampled k-space data of the actual imaging object to obtain PROPELLER undersampled CEST images corresponding to each ω value; and obtaining a CEST contrast image with the trained deep neural network and the PROPELLER undersampled CEST images.

In a preferred example, step S107 specifically includes: obtaining CEST images based on ω values and the $\sigma_k$, $\omega_k$, $A_k$ and $\delta$ parameter maps by a formula of the Lorentzian line shape model of CEST effect.

In a preferred example, step S108 specifically includes:

performing Fourier transformation on the CEST images corresponding to each ω value, to obtain corresponding k-space data;

where the k-space data of the CEST image corresponding to an ω value corresponds to a PROPELLER sampling blade of a particular sampling trajectory; each PROPELLER sampling blade collects several k-space lines of the corresponding CEST image; if there are M ω values, M sampling blades are present correspondingly; the angle of the first sampling blade is 0, and the difference between the angles of adjacent sampling blades is 180°/M, that is, 180°/M is taken as an increment for the angle of sampling blade; the angle of the sampling blade corresponding to the $m^{th}$ ω value is 180° (m−1)/M, and the sampling trajectory of M sampling blades spans a circle in the k-space.

The disclosure further provides a system for reconstruction of a CEST contrast image, including:

a training sample generating module configured to generate training samples for a deep neural network;

a network training module configured to train the deep neural network by using the training samples to obtain a trained deep neural network; and an image reconstruction module configured to reconstruct a CEST contrast image by using the trained deep neural network and PROPELLER undersampled CEST images;

where the training sample generating module specifically includes:

a simulated region obtaining unit configured to obtain a simulated region;

a geometric figure generating unit configured to randomly generate in the simulated region a geometric figure that serves to simulate a part of an imaging object;

a parameter setting unit configured to set parameters $\sigma_k$, $\omega_k$, $A_k$ and $\delta$ of the Lorentzian line shape model of CEST effect in the geometric figure to obtain a geometric figure with parameter $\sigma_k$, a geometric figure with parameter $\omega_k$, a geometric figure with parameter $A_k$, and a geometric figure with parameter $\delta$;

a texture and noise unit configured to add filtered texture values and noise to the geometric figure with parameter $\sigma_k$, the geometric figure with parameter $\omega_k$, the geometric figure with parameter $A_k$, and the geometric figure with parameter $\delta$, respectively, where the texture values are used to simulate the texture of the imaging object, and the noise is used to simulate the noise during MR sampling;

a parameter map generating unit configured to overlay the whole simulated region with the random geometric figures, to obtain $\sigma_k$, $\omega_k$, $A_k$ and $\delta$ parameter maps in the Lorentzian line shape model of CEST effect, respectively;

an ω value obtaining unit configured to obtain a combination of ω values in CEST imaging, where the combination of ω values is composed of a plurality of ω values, including a relatively large value corresponding to an unsaturated CEST image which is used for signal normalization;

a simulated CEST image generating unit configured to generate CEST images for each ω value by using the $\sigma_k$, $\omega_k$, $A_k$ and $\delta$ parameter maps in the Lorentzian line shape model of CEST effect;

a PROPELLE undersampling unit configured to perform PROPELLER undersampling on the CEST images;

a single training sample combining unit configured to combine the PROPELLER undersampled CEST images with the $A_k$ parameter map into a training sample; and a training sample generating unit configured to generate a preset quantity of training samples.

In a preferred example, the image reconstruction module specifically includes:

an actual data acquisition unit configured to acquire CEST image data from an actual imaging object with an MRI sequence to obtain PROPELLER undersampled k-space data at the saturation frequency offsets corresponding to each ω value in the combination of ω values;

an actual CEST image determining unit configured to perform Fourier transformation on the PROPELLER undersampled k-space data of the actual imaging object to obtain PROPELLER undersampled CEST images corresponding to each ω value; and a CEST contrast image determining unit configured to obtain a CEST contrast image from the PROPELLER undersampled CEST images with the trained deep neural network.

In a preferred example, the simulated CEST image generating unit obtains CEST images based on ω values and the $\sigma_k$, $\omega_k$, $A_k$ and $\delta$ parameter maps by a formula of the Lorentzian line shape model of CEST effect.

In a preferred example, the PROPELLE undersampling unit performs Fourier transformation on the CEST images corresponding to each ω value to obtain corresponding k-space data, where the k-space data of the CEST image corresponding to an ω value corresponds to a PROPELLER sampling blade of a particular sampling trajectory; each PROPELLER sampling blade collects several k-space lines of the corresponding CEST image; if there are M ω values, M sampling blade are present correspondingly; the angle of the first sampling blade is 0, and a difference between the angles of adjacent sampling blades is 180°/M, that is, 180°/M is taken as an increment for the angle of sampling blade (anticlockwise rotation relative to the horizontal direction); the angle of the sampling blade corresponding to the $m^{th}$ ω value is 180° (m−1)/M, and the sampling trajectory of M sampling blades spans a circle in the k-space.

Compared with the prior art, the disclosure has the following advantages:

Disclosed herein are a method and system for reconstruction of a CEST contrast image, which permit acceleration of CEST contrast imaging by PROPELLER undersampling and reconstruction of the CEST contrast image with a deep neural network, thereby greatly shortening the experimental time of a CEST imaging and the reconstruction time of a CEST contrast image and rendering the image smoother.

Moreover, the disclosure takes the influences of magnetization transfer (MT) effect, nuclear Overhauser effect (NOE), direct water saturation effect and inhomogeneous magnetic field effect on the CEST model into account, thus allowing for a more accurate reconstruction.

BRIEF DESCRIPTION OF THE DRAWINGS

To explain the technical solutions in examples of the disclosure or in the prior art more clearly, the accompanying drawings required in the examples will be described below in brief. Apparently, the accompanying drawings in the following description show merely some examples of the disclosure, and other drawings may be derived from these accompanying drawings by a person of ordinary skill in the art without creative efforts.

DETAILED DESCRIPTION

The technical solutions in the examples of the disclosure will be described below clearly and completely with reference to the accompanying drawings in the examples of the disclosure. Apparently, the described examples are merely a part rather than all of the examples of the disclosure. All other examples derived from the examples of the disclosure by a person of ordinary skill in the art without creative efforts shall fall within the protection scope of the disclosure.

The disclosure aims to provide a method and system for reconstruction of a CEST contrast image that can allow for reconstruction of a high-quality CEST contrast image from PROPELLER undersampled data and reduction of the time needed for a CEST experiment and the time for the reconstruction of the CEST contrast image.

To make the foregoing objective, features, and advantages of the disclosure clearer and more comprehensible, the disclosure will be further described in detail below with reference to the accompanying drawings and specific embodiments.

Figure 1:
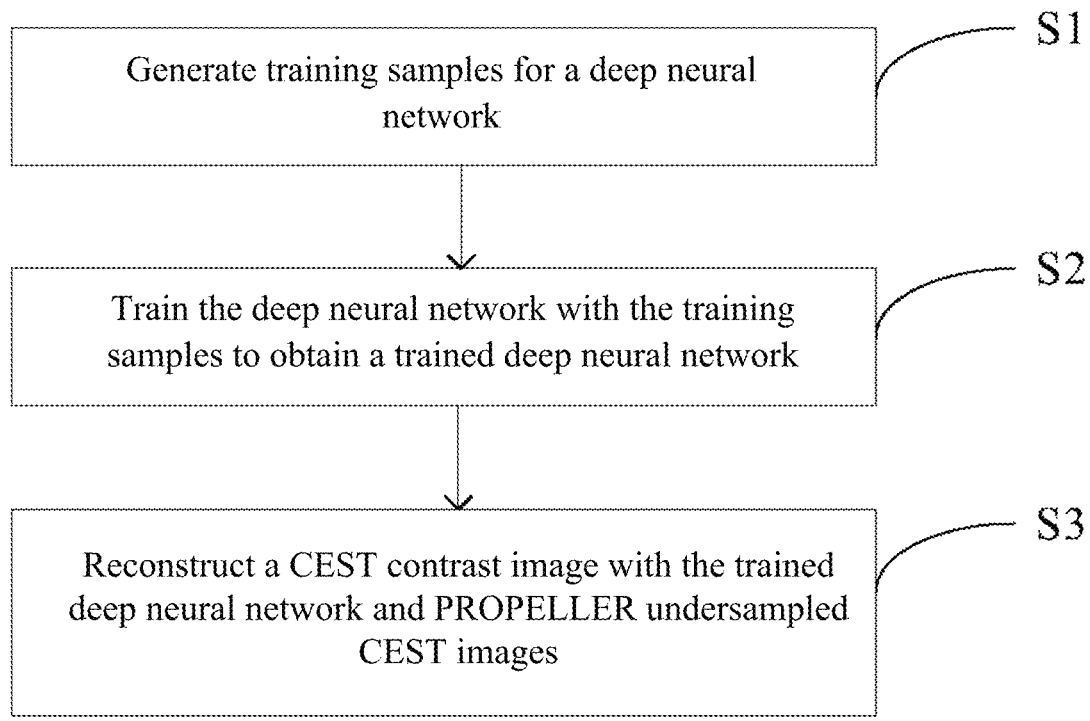
FIG. 1 is a flow chart of a method for reconstruction of a CEST contrast image according to an example of the disclosure.

As shown in FIG. 1 which is a flow chart of a method for reconstruction of a CEST contrast image according to an example of the disclosure, the disclosure provides a method for reconstruction of a CEST contrast image, including the following steps:

S1: generate training samples for a deep neural network.

S2: train the deep neural network by using the training samples to obtain a trained deep neural network.

S3: reconstruct a CEST contrast image by using the trained deep neural network and PROPELLER undersampled CEST images, which specifically includes:

acquire CEST image data from an actual imaging object with an MRI sequence to obtain PROPELLER undersampled k-space data at saturation frequency offsets corresponding to each ω value in a combination of ω values;

perform Fourier transformation on the PROPELLER undersampled k-space data of the actual imaging object to obtain PROPELLER undersampled CEST images corresponding to each ω value; and obtain the CEST contrast image with the trained deep neural network and the PROPELLER undersampled CEST images.

Figure 2:
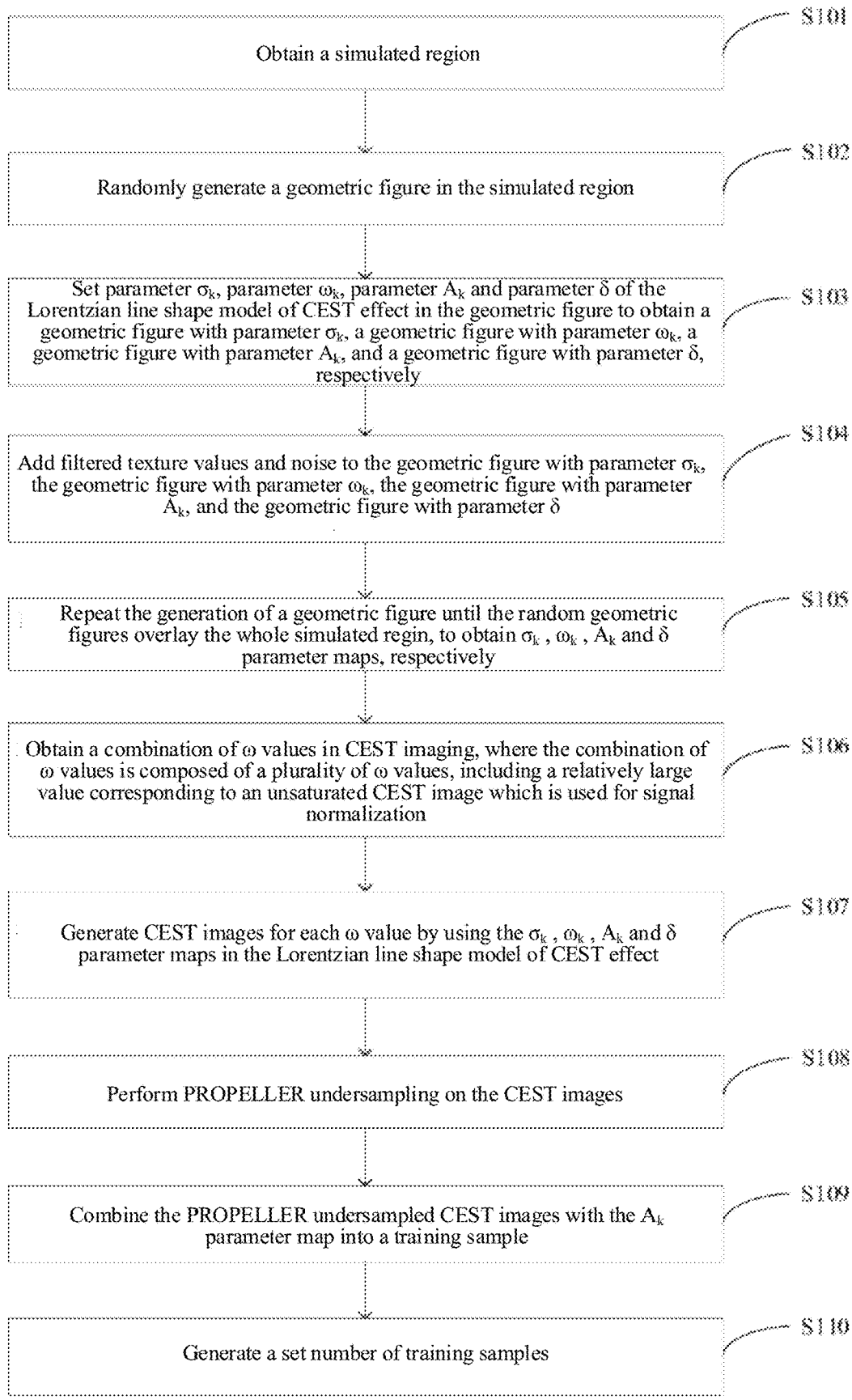
FIG. 2 is a flow chart of generating training samples for a deep neural network according to an example of the disclosure.

FIG. 2 is a flow chart of generating training samples for a deep neural network according to an example of the disclosure. As shown in FIG. 2, generating the training samples for the deep neural network specifically includes the following steps:

S101: obtain a simulated region;

S102: randomly generate in the simulated region a geometric figure that serves to simulate a part of an imaging object;

S103: set parameters $\sigma_k$, $\omega_k$, $A_k$ and $\delta$ of the Lorentzian line shape model of CEST effect in the geometric figure separately to obtain a geometric figure with parameter $\sigma_k$, a geometric figure with parameter $\omega_k$, a geometric figure with parameter $A_k$, and a geometric figure with parameter $\delta$;

S104: add filtered texture values and noise to the geometric figure with parameter $\sigma_k$, the geometric figure with parameter $\omega_k$, the geometric figure with parameter $A_k$, and the geometric figure with parameter $\delta$, respectively, where the texture values are used to simulate the texture of the imaging object, and the noise is used to simulate the noise during MR sampling;

S105: repeat S102 to S104 until the random geometric figures overlay the whole simulated region, to obtain $\sigma_k$, $\omega_k$, $A_k$ and $\delta$ parameter maps in the Lorentzian line shape model of CEST effect;

S106: obtain a combination of ω values in CEST imaging, where the combination of ω values is composed of a plurality of ω values, including a relatively large value corresponding to an unsaturated CEST image which is used for signal normalization;

S107: generate CEST images for each ω value by using the $\sigma_k$, $\omega_k$, $A_k$ and $\delta$ parameter maps in the Lorentzian line shape model of CEST effect;

S108: perform PROPELLER undersampling on the CEST images;

S109: combine the PROPELLER undersampled CEST images with the $A_k$ parameter map into a training sample; and S110: repeat S101 to S109 to generate a preset quantity of training samples.

Step S107 specifically includes: obtain CEST images based on ω values and the $\sigma_k$, $\omega_k$, $A_k$ and $\delta$ parameter maps by a formula of the Lorentzian line shape model of CEST effect. The formula of the Lorentzian line shape model of CEST effect is given below:

$$S(\omega)/S(0) = \sum_{k=1}^{n}\left[A_k\left(\frac{\sigma_k}{\sigma_k^2 + (\omega - \delta - \omega_k)^2}\right)\right], k = 1, 2, \ldots, n$$

where n is the number of concave peaks in Z-spectrum corresponding to the CEST images, such as the concave peak caused by MT effect, the concave peak caused by NOE and one or more concave peaks caused by CEST effect; k indicates the $k^{th}$ concave peak in Z-spectrum; ω is the frequency offset of a saturation pulse; S(ω) is the signal intensity when the saturation pulse corresponding to the ω value is applied; S(0) is the signal intensity when no saturation pulse is applied; $2\sigma_k$ is the full width at half maximum of the $k^{th}$ concave peak; $\omega_k$ is the nuclear spin resonance frequency corresponding to the $k^{th}$ concave peak; $A_k$ is the amplitude of the $k^{th}$ concave peak; and $\delta$ is the frequency offset caused by magnetic field inhomogeneity.

Step S108 specifically includes:

perform Fourier transformation on the CEST images corresponding to each ω value, to obtain corresponding k-space data.

The k-space data of the CEST image corresponding to an ω value corresponds to a PROPELLER sampling blade of a particular sampling trajectory. Each PROPELLER sampling blade collects several k-space lines of the corresponding CEST image. If there are M ω values, M sampling blades are present correspondingly. The angle of the first sampling blade is 0, and the difference between the angles of adjacent sampling blades is 180°/M. In other words, 180°/M is taken as an increment for the angle of sampling blade (anticlockwise rotation relative to the horizontal direction). The angle of the sampling blade corresponding to the $m^{th}$ ω value is 180° (m−1)/M, and the sampling trajectory of M sampling blades spans a circle in the k-space.

Figure 3:
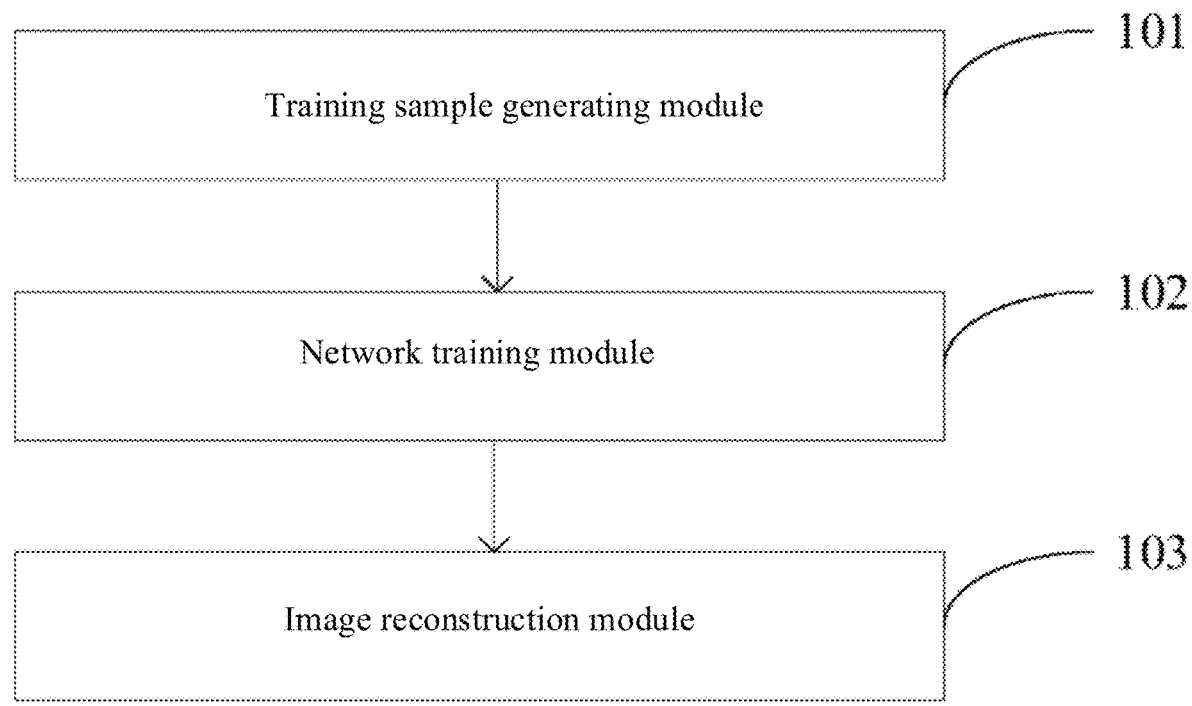
FIG. 3 is a structure diagram of a system for reconstruction of a CEST contrast image according to an example of the disclosure.

FIG. 3 is a structure diagram of a system for reconstruction of a CEST contrast image according to an example of the disclosure. The system specifically includes:

a training sample generating module 101 configured to generate training samples for a deep neural network;

a network training module 102 configured to train the deep neural network by using the training samples to obtain a trained deep neural network; and an image reconstruction module 103 configured to reconstruct a CEST contrast image by using the trained deep neural network and PROPELLER undersampled CEST images.

The training sample generating module 101 specifically includes:

a simulated region obtaining unit configured to obtain a simulated region;

a geometric figure generating unit configured to randomly generate in the simulated region a geometric figure that serves to simulate a part of an imaging object;

a parameter setting unit configured to set parameters $\sigma_k$, $\omega_k$, $A_k$ and $\delta$ of the Lorentzian line shape model of CEST effect in the geometric figure separately to obtain a geometric figure with parameter $\sigma_k$, a geometric figure with parameter $\omega_k$, a geometric figure with parameter $A_k$, and a geometric figure with parameter $\delta$;

a texture and noise unit configured to add filtered texture values and noise to the geometric figure with parameter $\sigma_k$, the geometric figure with parameter $\omega_k$, the geometric figure with parameter $A_k$, and the geometric figure with parameter $\delta$, respectively, where the texture values are used to simulate the texture of the imaging object, and the noise is used to simulate the noise during MR sampling;

a parameter map generating unit configured to overlay the whole simulated region with the random geometric figures, to obtain $\sigma_k$, $\omega_k$, $A_k$ and $\delta$ parameter maps in the Lorentzian line shape model of CEST effect;

an ω value obtaining unit configured to obtain a combination of ω values in CEST imaging, where the combination of ω values is composed of a plurality of ω values, including a relatively large value corresponding to an unsaturated CEST image which is used for signal normalization;

a simulated CEST image generating unit configured to generate CEST images for each ω value by using the $\sigma_k$, $\omega_k$, $A_k$ and $\delta$ parameter maps in the Lorentzian line shape model of CEST effect;

a PROPELLE undersampling unit configured to perform PROPELLER undersampling on the CEST images;

a single training sample combining unit configured to combine the PROPELLER undersampled CEST images with the $A_k$ parameter map into a training sample; and a training sample generating unit configured to generate a preset quantity of training samples.

The image reconstruction module 103 specifically includes:

an actual data acquisition unit configured to acquire CEST image data from an actual imaging object with an MRI sequence to obtain PROPELLER undersampled k-space data at saturation frequency offsets corresponding to each ω value in the combination of ω values;

an actual CEST image determining unit configured to perform Fourier transformation on the PROPELLER undersampled k-space data of the actual imaging object to obtain PROPELLER undersampled CEST images corresponding to each ω value; and a CEST contrast image determining unit configured to obtain the CEST contrast image with the trained deep neural network and the PROPELLER undersampled CEST images.

The simulated CEST image generating unit is specifically configured to:

obtain the CEST images based on ω values and the $\sigma_k$, $\omega_k$, $A_k$ and $\delta$ parameter maps by a formula of the Lorentzian line shape model of CEST effect. The formula of the Lorentzian line shape model of CEST effect is given below:

$$S(\omega)/S(0) = \sum_{k=1}^{n}\left[A_k\left(\frac{\sigma_k}{\sigma_k^2 + (\omega - \delta - \omega_k)^2}\right)\right], k = 1, 2, \ldots, n$$

where n is the number of concave peaks in Z-spectrum corresponding to the CEST images, such as the concave peak caused by MT effect, the concave peak caused by NOE and one or more concave peaks caused by CEST effect; k is the $k^{th}$ concave peak in Z-spectrum; ω is the frequency offset of a saturation pulse; S(ω) is the signal intensity when the saturation pulse corresponding to the ω value is applied; S(0) is the signal intensity when no saturation pulse is applied; $2\sigma_k$ is the full width at half maximum of the $k^{th}$ concave peak; $\omega_k$ is the nuclear spin resonance frequency corresponding to the $k^{th}$ concave peak; $A_k$ is the amplitude of the $k^{th}$ concave peak; and $\delta$ is the frequency offset caused by magnetic field inhomogeneity.

The PROPELLER undersampling unit is specifically configured to:

perform PROPELLER undersampling on the CEST images; and perform Fourier transformation on the CEST images corresponding to each ω value to obtain corresponding k-space data, where the k-space data of the CEST image corresponding to an ω value corresponds to a PROPELLER sampling blade of a particular sampling trajectory. Each PROPELLER sampling blade collects several k-space lines of the corresponding CEST image. If there are M ω values, M sampling blades are present correspondingly. The angle of the first sampling blades is 0, and the difference between the angles of adjacent sampling blades is 180°/M. In other words, 180°/M is taken as an increment for the angle of sampling blade (anticlockwise rotation relative to the horizontal direction). The angle of the sampling blade corresponding to the $m^{th}$ ω value is 180° (m−1)/M, and the sampling trajectory of M sampling blades spans a circle in the k-space.

Examples:

Step 1: generate training samples for a deep neural network. The process of generating the training samples specifically includes:

Step 1.1: obtain a simulated region;

Step 1.2: randomly generate a geometric figure in the simulated region, for example, generate a triangle, a rectangle, or a circle, where the position and size of the geometric figure are determined randomly;

Step 1.3: set parameter $\sigma_k$, $\omega_k$, $A_k$ and $\delta$ of the Lorentzian line shape model of CEST effect in the geometric figure to obtain geometric figures with respective parameters;

Step 1.4: add texture values filtered by Gaussian function and noise to the geometric figures obtained in step 1.3, where the texture values are used to simulate the texture of the imaging object, and the noise is used to simulate the noise during MR sampling;

Step 1.5: repeat steps 1.1-1.4 until the random geometric figures overlay the whole simulated region, to obtain $\sigma_k$, $\omega_k$, $A_k$ and $\delta$ parameter maps in the Lorentzian line shape model of CEST effect;

Step 1.6: obtain a combination of $\omega$ values in CEST imaging, where the combination of $\omega$ values is composed of a plurality of $\omega$ values, including a relatively large value corresponding to an unsaturated CEST image for signal normalization;

Step 1.7: generate CEST images for each $\omega$ value by using the $\sigma_k$, $\omega_k$, $A_k$ and $\delta$ parameter maps generated in step 1.5;

Step 1.8: perform PROPELLER undersampling on the CEST images generated in step 1.7;

Step 1.9: combine the PROPELLER undersampled CEST images with the $A_k$ parameter map into a training sample; and Step 1.10: repeat steps 1.1-1.9 to generate a preset quantity of training samples.

Step 2: train the deep neural network. The deep neural network is trained with the training samples generated in step 1.

Step 3: reconstruct a CEST contrast image from the PROPELLER undersampled CEST images of an actual imaging object with the deep neural network trained in step 2.

Preferably, in the step 1, a preferred simulated region has a matrix size of 128×128.

Preferably, in the step 1.2, the position and size of the geometric figure are determined randomly, and therefore, the geometric figures may overlap in the repetition process of step 1.2. In case of overlapping, overlaps may be removed by the way of set difference operation.

Preferably, in the step 1.3, MR parameters conform to the actual parameter distributions of the imaging object as much as possible. Preferred parameter values are as follows: for direct water saturation effect, $\omega_1$=0, $\sigma_1$ complies to uniform distribution in the range of [0.5 ppm, 2 ppm]; for amine protons, $\omega_2$=2 ppm, $\sigma_2$ complies to uniform distribution in the range of [0.3 ppm, 1.3 ppm]; for amide protons, $\omega_3$=3.5 ppm, $\sigma_3$ complies to uniform distribution in the range of [0.3 ppm, 1.3 ppm]; for MT effect, $\omega_4$=−2 ppm, $\sigma_4$ complies to uniform distribution in the range of [5 ppm, 20 ppm]; for NOE, $\omega_5$=−5 ppm, as complies to uniform distribution in the range of [1 ppm, 4 ppm]. Besides, $\delta$ complies to uniform distribution in the range of [−0.5 ppm, 0.5 ppm]; and $A_k$ (k=1-5) complies to uniform distribution in the range of [0, 1].

Preferably, in the step 2, the deep neural network is U-net.

Preferably, in the step 3, sampling on the imaging object is carried out with a CEST-PROPELLER sequence. Parameters are set as follows: field of view (FOV)=70 mm×70 mm, duration of saturation pulse=4000 ms, repetition time=5000 ms, echo train length=8, $\omega$ values=[−6, −5.5, −5, −4.5, −4, −3.5, −3, −2.5, −2, −1.5, −1, −0.5, 0, 0.5, 1, 1.5, 2, 2.5, 3, 3.5, 4, 4.5, 5, 5.5, 6, 100], total scanning time=7.8 min, and the number of sampling points in the frequency-encoding dimension and the number of sampling points in the phase-encoding dimension are 128 and 16, respectively. The sampled k-space data is expanded to 128×128 by zero filling, and then subjected to Fourier transformation, thereby obtaining the PROPELLER undersampled images. The images are input to the trained neutral network for reconstruction to obtain the CEST contrast image.

Figure 4:
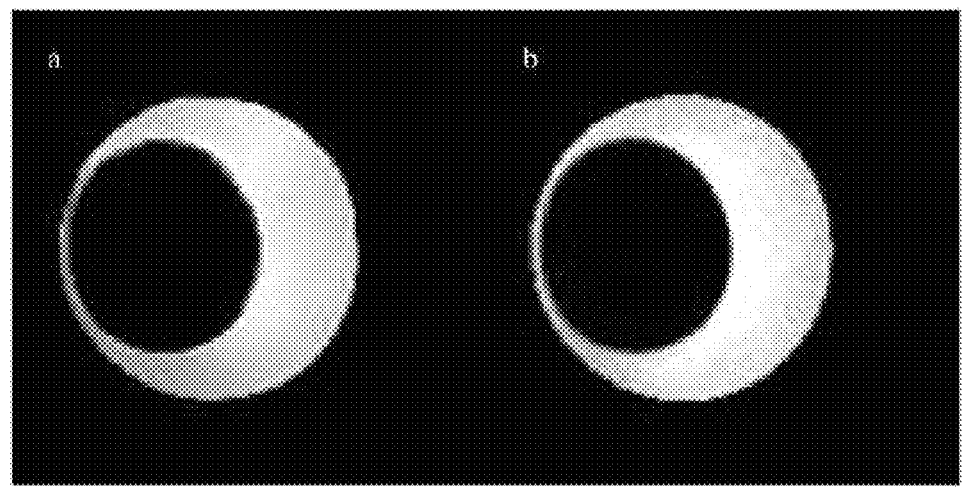
FIG. 4 shows a CEST contrast image of an egg reconstructed according to an example of the disclosure and a CEST contrast image resulting from calculation by a traditional method.

FIG. 4a shows a CEST contrast image of an egg reconstructed according to an example of the disclosure. As a contrast, FIG. 4b shows a CEST contrast image resulting from point-by-point Lorentzian fitting on fully sampled CEST images of CEST-FSE.

The CEST contrast image reconstruction based on U-Net convolutional neural network avoids point-by-point nonlinear fitting of original images. With regard to images having a sampling matrix of 128×128, this method can provide an acceleration factor of 8 for CEST imaging, and can obtain a smoother and more accurate CEST contrast image.

Different examples are described progressively herein. Each example focuses on the differences from other examples, and mutual reference may be made to the same and similar parts of such examples. Since the system corresponds to the method disclosed in the examples, the description thereof is relatively simple. For relevant information, reference may be made to the description of the method.

Specific examples are used herein to explain the principles and embodiments of the disclosure. The foregoing description of the examples is merely intended to help understand the method of the disclosure and its core ideas; besides, various modifications may be made by a person of ordinary skill in the art to specific embodiments and the scope of application in accordance with the ideas of the disclosure. In conclusion, the content of this specification shall not be construed as a limitation to the disclosure.

What is claimed is:

1. A method for reconstruction of a Chemical Exchange Saturation Transfer (CEST) contrast image, comprising:
    S1: generating training samples for a deep neural network, which specifically comprises the following steps:
        S101: obtaining a simulated region;
        S102: randomly generating in the simulated region a geometric figure that serves to simulate a part of an imaging object;
        S103: setting parameters $\sigma_k$, $\omega_k$, $A_k$ and $\delta$ of a Lorentzian line shape model of CEST effect in the geometric figure separately to obtain a geometric figure with parameter $\sigma_k$, a geometric figure with parameter $\omega_k$, a geometric figure with parameter $A_k$, and a geometric figure with parameter $\delta$;
        S104: adding filtered texture values and noise to the geometric figure with parameter $\sigma_k$, the geometric figure with parameter $\omega_k$, the geometric figure with parameter $A_k$, and the geometric figure with parameter $\delta$, wherein texture values are used to simulate a texture of the imaging object, and noise is used to simulate a noise during magnetic resonance (MR) sampling;
        S105: repeating S102 to S104 until random geometric figures overlay a whole simulated region, to obtain $\sigma_k$, $\omega_k$, $A_k$ and $\delta$ parameter maps in the Lorentzian line shape model of CEST effect, respectively;

S106: obtaining a combination of ω values in CEST imaging, wherein the combination of ω values is composed of a plurality of ω values, comprising a relatively large value corresponding to an unsaturated CEST image which is used for signal normalization;

S107: generating CEST images for each ω value by using the $\sigma_k$, $\omega_k$, $A_k$ and δ parameter maps in the Lorentzian line shape model of CEST effect;

S108: performing PROPELLER undersampling on the CEST images;

S109: combining the PROPELLER undersampled CEST images with an $A_k$ parameter map into a training sample; and S110: repeating S101 to S109 to generate a preset quantity of training samples;

S2: training the deep neural network by using the training samples to obtain a trained deep neural network; and S3: reconstructing a CEST contrast image by using the trained deep neural network and PROPELLER undersampled CEST images, which specifically comprises the following steps:

acquiring CEST image data from an actual imaging object with a magnetic resonance imaging (MRI) sequence to obtain PROPELLER undersampled k-space data at saturation frequency offsets corresponding to each ω value in the combination of ω values;

performing Fourier transformation on the PROPELLER undersampled k-space data of the actual imaging object to obtain PROPELLER undersampled CEST images corresponding to each ω value; and obtaining a CEST contrast image with the trained deep neural network and the PROPELLER undersampled CEST images.

2. The method for reconstruction of a CEST contrast image according to claim 1, wherein step S107 specifically comprises: obtaining CEST images based on ω values and the $\sigma_k$, $\omega_k$, $A_k$ and δ parameter maps by a formula of the Lorentzian line shape model of CEST effect.

3. The method for reconstruction of a CEST contrast image according to claim 1, wherein step S108 specifically comprises:

performing Fourier transformation on the CEST images corresponding to each ω value, to obtain corresponding k-space data;

wherein the k-space data of the CEST image corresponding to an ω value corresponds to a PROPELLER sampling blade of a particular sampling trajectory; each PROPELLER sampling blade collects several k-space lines of the corresponding CEST image; if there are M ω values, M sampling blades are present correspondingly; the angle of the first sampling blade is 0, and the difference between the angles of adjacent sampling blades is 180°/M, that is, 180°/M is taken as an increment for the angle of sampling blade; the angle of the sampling blade corresponding to the $m^{th}$ ω value is 180° (m−1)/M, and the sampling trajectory of M sampling blades spans a circle in the k-space.

4. A system for reconstruction of a CEST contrast image, comprising:

a training sample generating module configured to generate training samples for a deep neural network;

a network training module configured to train the deep neural network by using the training samples to obtain a trained deep neural network; and an image reconstruction module configured to reconstruct a CEST contrast image by using the trained deep neural network and PROPELLER undersampled CEST images;

wherein the training sample generating module specifically comprises:

a simulated region obtaining unit configured to obtain a simulated region;

a geometric figure generating unit configured to randomly generate in the simulated region a geometric figure that serves to simulate a part of an imaging object;

a parameter setting unit configured to set parameters $\sigma_k$, $\omega_k$, $A_k$ and δ of the Lorentzian line shape model of CEST effect in the geometric figure to obtain a geometric figure with parameter $\sigma_k$, a geometric figure with parameter $\omega_k$, a geometric figure with parameter $A_k$, and a geometric figure with parameter δ;

a texture and noise unit configured to add filtered texture values and noise to the geometric figure with parameter $\sigma_k$, the geometric figure with parameter $\omega_k$, the geometric figure with parameter $A_k$, and the geometric figure with parameter δ, respectively, wherein the texture values are used to simulate the texture of the imaging object, and the noise is used to simulate the noise during MR sampling;

a parameter map generating unit configured to overlay the whole simulated region with the random geometric figures, to obtain $\sigma_k$, $\omega_k$, $A_k$ and δ parameter maps in the Lorentzian line shape model of CEST effect, respectively;

an ω value obtaining unit configured to obtain a combination of ω values in CEST imaging, wherein the combination of ω values is composed of a plurality of ω values, comprising a relatively large value corresponding to an unsaturated CEST image which is used for signal normalization;

a simulated CEST image generating unit configured to generate CEST images for each ω value by using the $\sigma_k$, $\omega_k$, $A_k$ and δ parameter maps in the Lorentzian line shape model of CEST effect;

a PROPELLER undersampling unit configured to perform PROPELLER undersampling on the CEST images;

a single training sample combining unit configured to combine the PROPELLER undersampled CEST images with the $A_k$ parameter map into a training sample; and a training sample generating unit configured to generate a preset quantity of training samples.

5. The system for reconstruction of a CEST contrast image according to claim 4, wherein the image reconstruction module specifically comprises:

an actual data acquisition unit configured to acquire CEST image data from an actual imaging object with an MRI sequence to obtain PROPELLER undersampled k-space data at saturation frequency offsets corresponding to each ω value in the combination of ω values;

an actual CEST image determining unit configured to perform Fourier transformation on the PROPELLER undersampled k-space data of the actual imaging object to obtain PROPELLER undersampled CEST images corresponding to each ω value; and a CEST contrast image determining unit configured to obtain a CEST contrast image from the PROPELLER undersampled CEST images with the trained deep neural network.

6. The system for reconstruction of a CEST contrast image according to claim 4, wherein the simulated CEST image generating unit obtains CEST images based on $\omega$ values and the $\sigma_k$, $\omega_k$, $A_k$ and $\delta$ parameter maps by a formula of the Lorentzian line shape model of CEST effect.

7. The system for reconstruction of a CEST contrast image according to claim 4, wherein the PROPELLER undersampling unit performs Fourier transformation on the CEST images corresponding to each $\omega$ value to obtain corresponding k-space data, wherein the k-space data of the CEST image corresponding to an $\omega$ value corresponds to a PROPELLER sampling blade of a particular sampling trajectory; each PROPELLER sampling blade collects several k-space lines of the corresponding CEST image; if there are M $\omega$ values, M sampling blades are present correspondingly; the angle of the first sampling blade is 0, and a difference between the angles of adjacent sampling blades is 180°/M, that is, 180°/M is taken as an increment for the angle of sampling blade; the angle of the sampling blade corresponding to the $m^{th}$ $\omega$ value is 180° (m−1)/M, and the sampling trajectory of M sampling blades spans a circle in the k-space.

* * * * *